United States Patent
Katcha et al.

(10) Patent No.: US 7,957,786 B2
(45) Date of Patent: Jun. 7, 2011

(54) METHODS AND APPARATUS FOR COMMUNICATING SIGNALS BETWEEN PORTIONS OF AN APPARATUS IN RELATIVE MOVEMENT TO ONE ANOTHER

(75) Inventors: Jason Stuart Katcha, Whitefish Bay, WI (US); Nathanael Dale Huffman, Mishawaka, IN (US); James K. Omick, New Berlin, WI (US); Phil E. Pearson, Jr., Hartland, WI (US)

(73) Assignee: General Electric Company, Schenectady, NY (US)

( * ) Notice: Subject to any disclaimer, the term of this patent is extended or adjusted under 35 U.S.C. 154(b) by 1667 days.

(21) Appl. No.: 11/204,208

(22) Filed: Aug. 15, 2005

(65) Prior Publication Data

US 2007/0035883 A1    Feb. 15, 2007

(51) Int. Cl.
*A61B 5/055*     (2006.01)
*H05G 1/10*      (2006.01)
*H05G 1/02*      (2006.01)
*H01F 21/02*     (2006.01)

(52) U.S. Cl. ......... 600/407; 378/101; 378/197; 336/145

(58) Field of Classification Search .......... 600/407, 600/410–411; 382/131; 378/15, 101, 197; 323/362, 358; 360/281.8; 336/145, 182; 455/39

See application file for complete search history.

(56) References Cited

U.S. PATENT DOCUMENTS

| | | | |
|---|---|---|---|
| 4,160,973 A | | 7/1979 | Berlin, Jr. |
| 4,225,851 A | * | 9/1980 | Reschovsky et al. ..... 340/870.04 |
| 4,912,735 A | * | 3/1990 | Beer .............................. 378/15 |
| 5,175,754 A | | 12/1992 | Casey et al. |
| 5,469,488 A | | 11/1995 | Ono |
| 5,521,144 A | * | 5/1996 | Farr et al. ...................... 504/215 |
| 5,530,425 A | | 6/1996 | Harrison |
| 5,577,026 A | * | 11/1996 | Gordon et al. ................. 370/278 |
| 5,594,176 A | * | 1/1997 | Kiefer ............................. 73/623 |
| 5,608,771 A | * | 3/1997 | Steigerwald et al. .......... 378/15 |
| 5,740,222 A | | 4/1998 | Fujita et al. |
| 5,748,696 A | | 5/1998 | Fujita et al. |

(Continued)

FOREIGN PATENT DOCUMENTS

CN    1139993 A    1/1997

OTHER PUBLICATIONS

Chinese Patent Office, Second Office Action and Text of Second Office Action for Application No. 200610115511.3, Jul. 20, 2010, 12 pages, CN.

*Primary Examiner* — Long V Le
*Assistant Examiner* — Katherine L Fernandez
(74) *Attorney, Agent, or Firm* — Armstrong Teasdale LLP (57) ABSTRACT

A data transmission system that includes a transmitter; a receiver; and a magnetically coupled rotary transformer having a first portion and a second portion in moveable relationship with one another. The transmitter is electrically and mechanically coupled to the first portion of the rotary transformer, and the receiver is electrically and mechanically coupled to the second portion of the rotary transformer. The transmitter and the receiver are configured to wirelessly communicate data across the rotary transformer while the first and the second portions of the rotary transformer are in relative rotary motion.

20 Claims, 7 Drawing Sheets

U.S. PATENT DOCUMENTS

| | | |
|---|---|---|
| 5,848,126 A | 12/1998 | Fujita et al. |
| 6,181,766 B1 | 1/2001 | Pearson, Jr. et al. |
| 6,203,196 B1 | 3/2001 | Meyer et al. |
| 6,292,919 B1 | 9/2001 | Fries et al. |
| 6,301,324 B1 | 10/2001 | Pearson, Jr. et al. |
| 6,480,561 B1 | 11/2002 | Proksa |
| 6,512,437 B2 * | 1/2003 | Jin et al. .................. 336/178 |
| 6,602,185 B1 | 8/2003 | Uchikubo |
| 6,759,759 B2 * | 7/2004 | Kojima et al. ............... 307/10.1 |
| 6,955,671 B2 | 10/2005 | Uchikubo |
| 7,194,062 B2 | 3/2007 | Balan et al. |
| 7,436,924 B2 | 10/2008 | Takahashi et al. |
| 2003/0185427 A1 | 10/2003 | Hsieh et al. |
| 2004/0116797 A1 | 6/2004 | Takahashi et al. |
| 2005/0135551 A1 | 6/2005 | Katcha et al. |
| 2005/0226380 A1 | 10/2005 | Katcha et al. |

\* cited by examiner

FIG. 12

METHODS AND APPARATUS FOR COMMUNICATING SIGNALS BETWEEN PORTIONS OF AN APPARATUS IN RELATIVE MOVEMENT TO ONE ANOTHER

BACKGROUND OF THE INVENTION

This invention relates generally to data communication, and more particularly, to data communication across a moving interface such as, for example, a rotating gantry of a computed tomographic (CT) imaging system.

In some known CT imaging system configurations, an x-ray source projects a fan-shaped beam which is collimated to lie within an X-Y plane of a Cartesian coordinate system and generally referred to as an "imaging plane". The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurements from all the detectors are acquired separately to produce a transmission profile.

In third generation CT systems, the x-ray source and the detector array are rotated with a gantry within the imaging plane and around the object to be imaged such that the angle at which the x-ray beam intersects the object constantly changes. A group of x-ray attenuation measurements, i.e., projection data, from the detector array at one gantry angle is referred to as a "view". A "scan" of the object comprises a set of views made at different gantry angles, or view angles, during one revolution of the x-ray source and detector.

In an axial scan, the projection data is processed to construct an image that corresponds to a two-dimensional slice taken through the object. One method for reconstructing an image from a set of projection data is referred to in the art as the filtered backprojection technique. This process converts the attenuation measurements from a scan into integers called "CT numbers" or "Hounsfield units" (HU), which are used to control the brightness of a corresponding pixel on a cathode ray tube display.

To reduce the total scan time, a "helical" scan may be performed. To perform a "helical" scan, the patient is moved while the data for the prescribed number of slices is acquired. Such a system generates a single helix from a fan beam helical scan. The helix mapped out by the fan beam yields projection data from which images in each prescribed slice may be reconstructed.

Reconstruction algorithms for helical scanning typically use helical weighing algorithms that weight the collected data as a function of view angle and detector channel index. Specifically, prior to a filtered backprojection process, the data is weighted according to a helical weighing factor, which is a function of both the gantry angle and detector angle. The weighted data is then processed to generate CT numbers and to construct an image that corresponds to a two-dimensional slice taken through the object.

To further reduce the total acquisition time, multi-slice CT has been introduced. In multi-slice CT, multiple rows of projection data are acquired simultaneously at any time instant. When combined with helical scan mode, the system generates a single helix of cone beam projection data. Similar to the single slice helical, weighting scheme, a method can be derived to multiply the weight with the projection data prior to the filtered backprojection algorithm.

In at least one known CT imaging system, a low speed communication between stationary electronics and rotating electronics utilizes a set of conducting brushes that allow an electrical connection from the stationary side to the rotating side. This architecture is simple and easy to implement because it allows power to also be transferred using brushes and conducting rings.

However, brushes eventually wear down need to be replaced by service personnel to ensure proper conductivity across the ring. Also, brush-based system require regular preventative maintenance to remove conducting brush dust from the system to prevent communication and power failures.

BRIEF DESCRIPTION OF THE INVENTION

In one aspect, the present invention therefore provides an imaging system configured to acquire an image of an object utilizing a rotating gantry and having a stationary electronic system and a rotating electronic system that rotates with the rotating gantry. The imaging system further includes a magnetically coupled rotary transformer with a magnetic core having both a stationary portion and a rotating portion. The rotating electronic system is electrically and mechanically coupled to the rotating portion of the rotary transformer and the stationary electronic system is electrically and mechanically coupled to the stationary portion of the rotary transformer. The rotating electronic system and stationary electronic system are configured to wirelessly communicate data across the rotary transformer.

In another aspect, the present invention provides a data transmission system that includes a transmitter; a receiver; and a magnetically coupled rotary transformer having a first portion and a second portion in moveable relationship with one another. The transmitter is electrically and mechanically coupled to the first portion of the rotary transformer, and the receiver is electrically and mechanically coupled to the second portion of the rotary transformer. The transmitter and the receiver are configured to wirelessly communicate data across the rotary transformer while the first and the second portions of the rotary transformer are in relative rotary motion.

In yet another aspect, the present invention provides a method for transferring data. The method includes electrically and mechanically coupling a first electronic system to a first portion of a magnetically coupled rotary transformer and electrically and mechanically coupling a second electronic system to a second portion of the rotary transformer. The method further includes wirelessly communicating data between the first and the second electronic systems across the rotary transformer while the first and the second portions of the rotary transformer are in relative motion.

It can thus be appreciated that service and repair costs of sliprings in rotating systems such as a CT imaging system can be mitigated using various configurations of the present invention. Configurations of the present invention are useful in various types of imaging systems, such as nuclear magnetic resonance (NMR) imaging systems and ultrasonic imaging systems. Configurations of the present invention are also useful in many other types of electronic equipment (not necessarily imaging systems) in which data or data and power must be transmitted across a rotational interface.

DETAILED DESCRIPTION OF THE INVENTION

As used herein, an element or step recited in the singular and proceeded with the word "a" or "an" should be understood as not excluding plural said elements or steps, unless such exclusion is explicitly recited. Furthermore, references to "one embodiment" of the present invention are not intended to be interpreted as excluding the existence of additional embodiments that also incorporate the recited features.

Also as used herein, the phrase "reconstructing an image" is not intended to exclude embodiments of the present invention in which data representing an image is generated but a viewable image is not. However, many embodiments generate (or are configured to generate) at least one viewable image.

Figure 1:
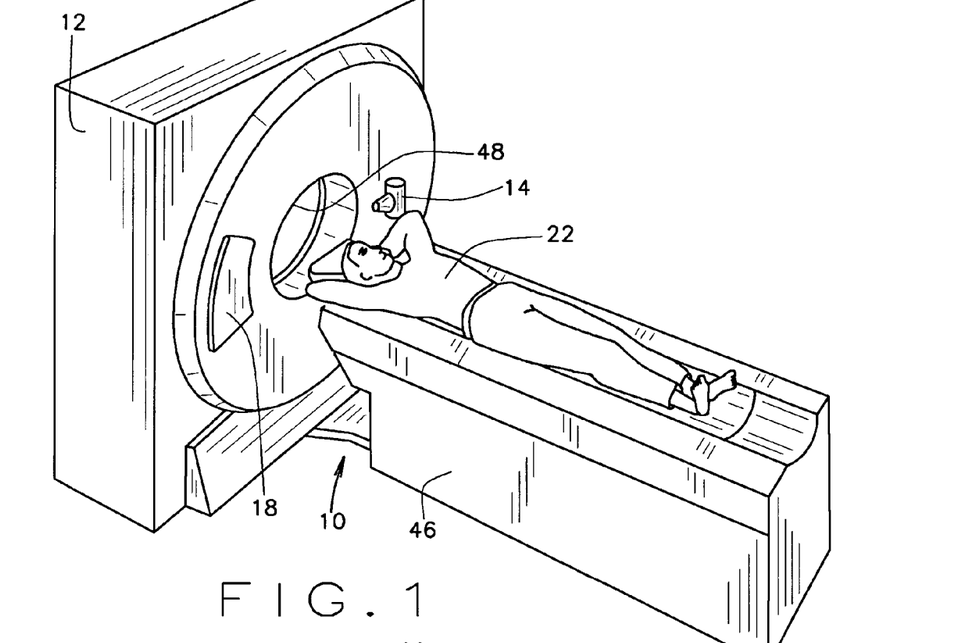
FIG. 1 is a pictorial drawing of a configuration of a computed tomographic (CT) imaging system employing a rotating gantry.
Figure 2:
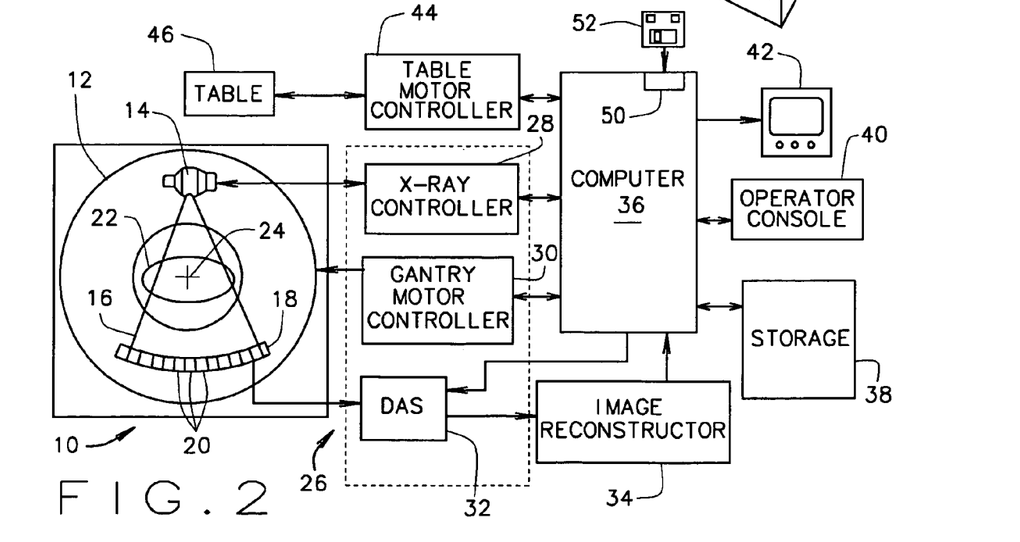
FIG. 2 is a block diagram of the CT imaging system of FIG. 1.

Referring to FIGS. 1 and 2, a multi-slice scanning imaging system, for example, a Computed Tomography (CT) imaging system 10, is shown as including a gantry 12 representative of a "third generation" CT imaging system. Gantry 12 has a radiation source 14, for example, an x-ray tube (also called x-ray source 14 herein) that projects a beam of radiation such as x-rays 16 toward a detector array 18 on the opposite side of gantry 12. Detector array 18 is formed by a plurality of detector rows (not shown) including a plurality of detector elements 20 which together sense the projected x-rays that pass through an object, such as a medical patient 22 between array 18 and source 14. Each detector element 20 produces an electrical signal that represents the intensity of an impinging x-ray beam and hence can be used to estimate the attenuation of the beam as it passes through object or patient 22. During a scan to acquire x-ray projection data, gantry 12 and the components mounted therein rotate about a center of rotation 24. FIG. 2 shows only a single row of detector elements 20 (i.e., a detector row). However, multi-slice detector array 18 includes a plurality of parallel detector rows of detector elements 20 such that projection data corresponding to a plurality of quasi-parallel or parallel slices can be acquired simultaneously during a scan.

Rotation of components on gantry 12 and the operation of x-ray source 14 are governed by a control mechanism 26 of CT system 10. Control mechanism 26 includes an x-ray controller 28 that provides power and timing signals to x-ray source 14 and a gantry motor controller 30 that controls the rotational speed and position of components on gantry 12. A data acquisition system (DAS) 32 in control mechanism 26 samples analog data from detector elements 20 and converts the data to digital signals for subsequent processing. An image reconstructor 34 receives sampled and digitized x-ray data from DAS 32 and performs high-speed image reconstruction. The reconstructed image is applied as an input to a computer 36, which stores the image in a storage device 38. Image reconstructor 34 can be specialized hardware or computer programs executing on computer 36.

Computer 36 also receives commands and scanning parameters from an operator via console 40 that has a keyboard. An associated cathode ray tube display, liquid crystal display, plasma display, or other suitable display 42 allows the operator to observe the reconstructed image and other data from computer 36. The operator supplied commands and parameters are used by computer 36 to provide control signals and information to DAS 32, x-ray controller 28, and gantry motor controller 30. In addition, computer 36 operates a table motor controller 44, which controls a motorized table 46 to position patient 22 in gantry 12. Particularly, table 46 moves portions of patient 22 through gantry opening 48.

Because of the rotation of gantry 12, electronic signals and/or power must be coupled between components on moving gantry 12 and a stationary portion of imaging system 10. For example, data generated by detector array 18 on rotating gantry 12 must be electronically transferred to DAS 32, which is located in a stationary portion of imaging system 10 during the rotation of gantry 12. Simultaneously, power must be transferred from a power supply (not shown in FIGS. 1 and 2) located in a stationary portion of imaging system 10 to radiation source 14 so that it can generate radiation 16 while gantry 12 is rotating.

Figure 3:
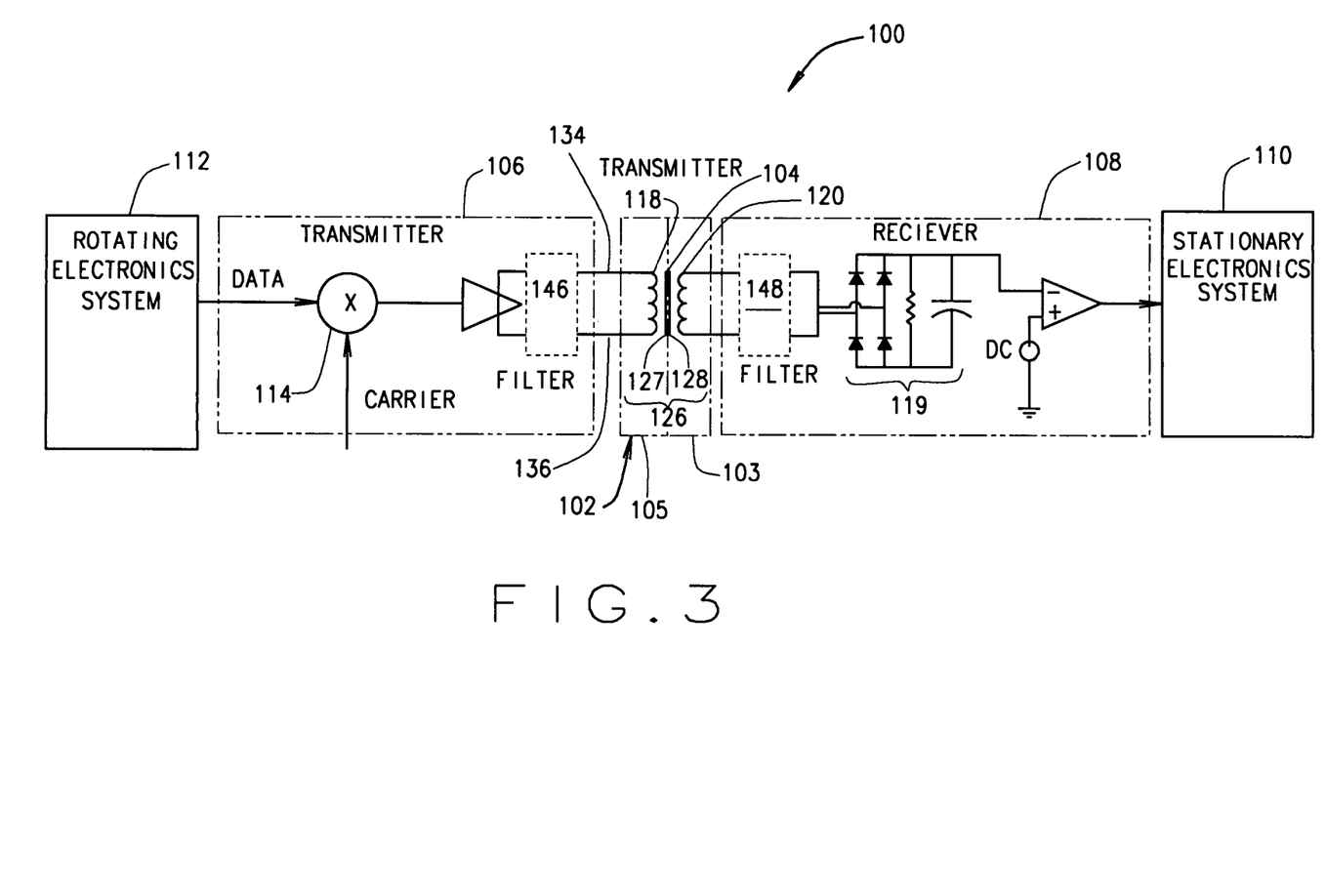
FIG. 3 is a schematic block diagram of a configuration of a contactless communication system.

In some configurations of the present invention and referring to FIG. 3, to mitigate service and repair costs of sliprings in imaging systems such as CT imaging systems 10, a contactless communication system 100 is provided. More particularly, data is transferred across a rotary transformer 102 having a gap 104 using a transmitter 106, a receiver 108. In some configurations, gap 104 is an air gap (better seen in FIG. 4) between parts 127, 128 of a magnetic core 126 of transformer 102. Communication is provided between a stationary electronics system 110 and a rotating electronics system 112. The communication can be one way, in the sense illustrated in FIG. 3, or can be in the opposite direction (by reversing the positions of transmitter 106 and receiver 108). Bidirectional communication is also possible by using transceivers on both sides of transformer 102. For example, in some configurations, transmitter 106 is a portion of a transceiver, and receiver 108 is a portion of another, separate transceiver. Thus, without loss of generality, it will be sufficient herein to describe a one-way data transmission system. Also, it will be understood that the designation of "stationary" and "rotating" is somewhat arbitrary, inasmuch as motion is relative and in some configurations there may not be a preferred stationary frame of reference. In such configurations, either side can be considered as moving relative to the other side, and it may be convenient to refer to electronics systems 110 and 112 as "first" and "second" electronic systems, in whatever order is convenient. In configurations in which rotary transformer 102 is mounted on a gantry of a CT imaging system 10, it may be more convenient to adopt the floor supporting imaging system 10 as a stationary frame of reference.

In some configurations of the present invention and referring to FIG. 3, transmitter 106 includes a modulator 114 (such as an radio frequency modulator) that modulates a data stream onto a carrier frequency to facilitate transfer across rotary transformer 102. In some configurations, for example, the data stream is a 2.5 Mbaud data stream that is amplitude modulated onto a 10 MHz sine wave. The modulated signal is coupled across an air gap 104 (best seen in FIG. 4) of transformer 102. to receiver 108, which includes a demodulator 119 to recover the data stream. In some configurations, demodulator 119 is a full wave rectifier configured to demodulate the original data. The data is communicated across transformer 102 while transformer 102 is rotating.

In various configurations, one or more other forms of modulation are used in place of or in addition to amplitude modulation. A non-exhaustive list of such other forms of modulation include frequency modulation, phase shift keying, frequency shift keying, pulse width modulation, and various combinations thereof. Also, in some configurations, the carrier frequency is phased with the data at transmitter 106 to minimize waveform jitter at receiver 108.

Figure 4:
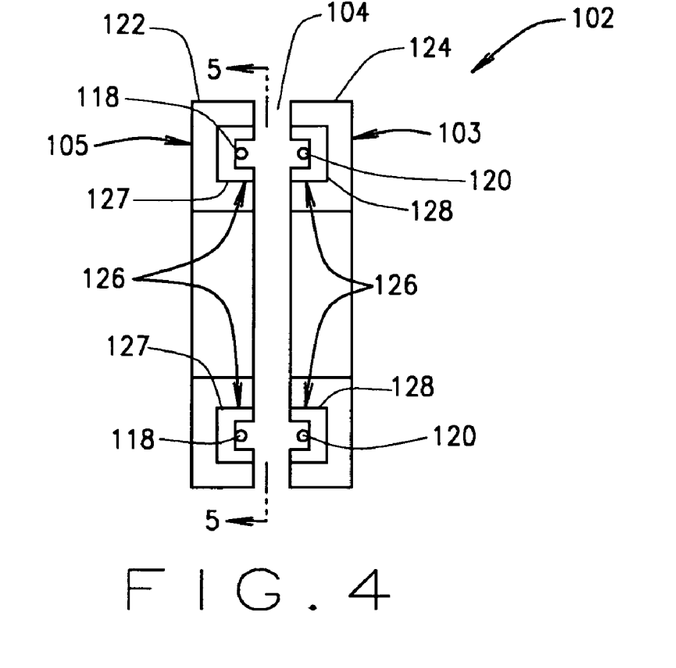
FIG. 4 is a sectional slice view of the rotary transformer configuration of FIG. 3.
Figure 5:
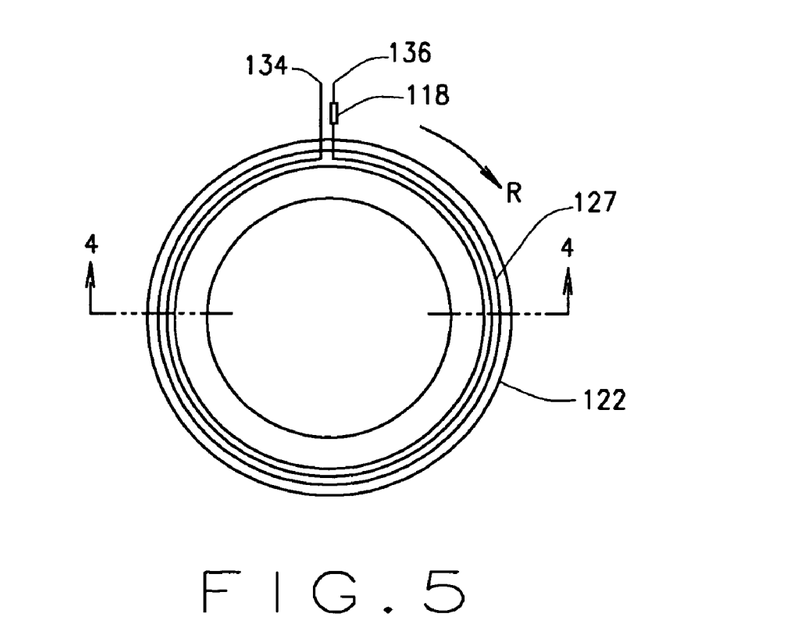
FIG. 5 is a view of one half of the rotary transformer of FIG. 4, taken along line 5-5 in FIG. 4. Line 4-4 is illustrative of a slice used to show the sectional slice view of FIG. 4.

Referring to FIGS. 3, 4, and 5, rotary transformer 102 couples the carrier frequency modulated with the data stream across air gap 104 to wirelessly communicate data across magnetically coupled rotary transformer 102 while allowing windings 118, 120 (representing a primary winding and a secondary winding) to move with respect to one other. For example, ring 122 rotates in a direction R shown in FIG. 5, taking a first winding winding 118 and magnetic core portion 127 along with it, while ring 124, and hence a second winding 120, remains stationary.

In some configurations, rotary transformer 102 comprises a pair of plastic or other nonconductive rings 122, 124 separated by an air gap 104. Rings 122, 124 are large enough in some configurations to encircle a patient 22, such as the patient shown in FIG. 1, need not be in all configurations. A magnetic core 126 such as a ferrite core is embedded in plastic rings 122 and 124. One part or portion 127 of magnetic core 126 is embedded in plastic ring 122 and an opposing part or portion 128 of magnetic core 126 is embedded in plastic ring 124. Each part 127, 128 of magnetic core 126 is circular in shape and has a cross section that allows embedding of at least one conductive winding (e.g., a copper winding) 118 or 120. For example, magnetic core parts 127, 128 have either a C-shaped cross-section as shown, or an E-shaped cross-section. Winding 118 or 120 is wound within the concave part of the C-shaped (or E-shaped) cross section. Ends 134, 136 of winding 118 exit from magnetic core part 127 and ring 122 as shown in FIG. 5. Ring 124 is similarly constructed with core part 128 and winding 120. In some configurations, holes and/or channels (not shown in FIG. 5) are provided in the magnetic core parts and/or the plastic rings to facilitate placement of the ends of the windings.

As indicated above, the labels "rotating" and "stationary" may be considered somewhat arbitrary in that, in some configurations (and when considering some configurations of transformer 102 by itself), it is more convenient to use labels explicitly recognizing the relative nature of the motion. However, in some configurations, it can usefully be said that core part 127 and winding 118 comprise a rotating portion of magnetically coupled rotary transformer 102 and that core part 128 and winding 120 comprise stationary portion of magnetically coupled rotary transformer 102. It can also be convenient to refer to transformer 102 as having a first magnetic core portion 127 and a second magnetic core portion 128, with these portions being in moveable relationship therebetween. In those cases, first and second core portions 127 and 128, respectively, can be said to be in relative motion when in use.

In some configurations of the present invention, stationary electronics system 110 is mechanically and electrically coupled to a stationary portion 103 of transformer 102. For example, stationary electronics system 110 comprises a stationary portion of the electronics of imaging system 10, and stationary portion of 103 of transformer 102 and the stationary portion of the electronics of imaging system 10 are both mechanically coupled to the base of imaging system 10. Rotating electronics system 112 is mechanically and electrically coupled to a rotating portion 105 of transformer 102. For example, rotating electronics system 112 is mechanically coupled to gantry 12 of imaging system 10, which is also mechanically coupled to rotating portion 105 of transformer 102. In some configurations, data is or can be transferred from rotating electronics system 112 across transformer 102 to stationary electronics system 110 while stationary portion 103 and rotating portion 105 are in relative motion. (The invention does not exclude configurations in which data is or can also be transferred while portions 103 and 105 are not in relative motion.) In some configurations, such as that shown in FIG. 3, rotating electronics system 112 is electrically and mechanically coupled to transmitter 106, which itself is electrically and mechanically coupled to rotating portion 105 of transformer 102. Similarly, stationary electronics system 110 is electrically and mechanically coupled to receiver 108, which itself is electrically and mechanically coupled to stationary portion 103 of transformer 102. However, the invention does not limit transmission either to a single direction nor exclusively to the direction shown in FIG. 3. Moreover, a different frame of reference than that used for the motion labels in this example can be used, in which case, different motion labels may be applied to the various components.

Figure 6:
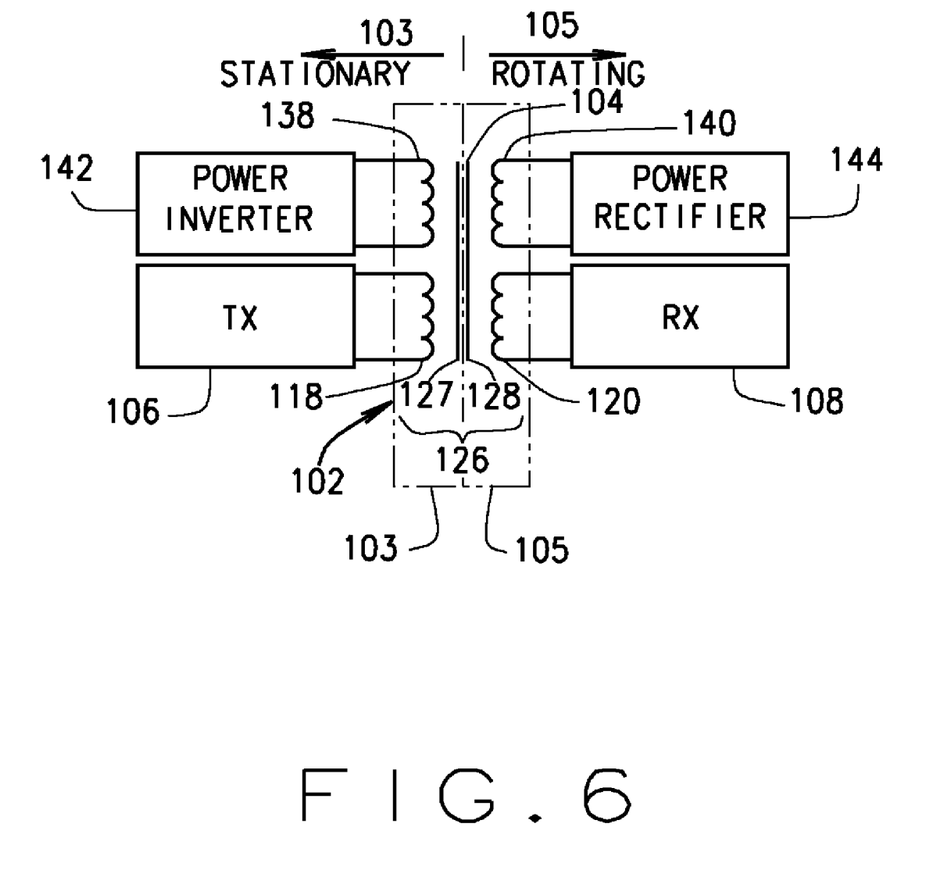
FIG. 6 is a block schematic diagram of a rotary transformer and associated electronics configured to transmit both power and data through the rotary transformer.

In some configurations and referring to FIG. 6, a rotary transformer 102 used for data transmission shares its magnetic core 126 with a power transmission system comprising, for example, a power inverter 142 and a power rectifier 144. For example, two windings 118, 138, and 120, 140 are present on each core portions 127 and 128, respectively. Windings 118 and 120 are configured to transfer data, as in the various configurations represented by FIG. 3, whereas windings 138 and 140 are configured to transfer power from a power supply or inverter 142 across air gap 104 to a power rectifier 144. In many configurations, power is transmitted at a significantly different frequency than the carrier frequency on which the data is modulated. For example, in some configurations, power is transmitted at a lower AC frequency (by way of non-exhaustive example only, 100 kHz or at a frequency less than 200 kHz). Data is transmitted at a higher carrier frequency (by way of non-exhaustive example only, 10 MHz or on a frequency greater than 5 MHz, or on a frequency greater than 1 MHz). Thus, a power component imposed on data windings 118 and 120 can be removed or reduced using at least a high-pass or band-pass filter 148, or high-pass or band-pass filters 146 and 148 shown in FIG. 3. In other configurations, it is possible for the carrier frequency to be less than or even equal to the power frequency. Thus, frequencies used for power and RF carrier and the design of filters 146 and 148, if used, can be left to a circuit designer as design choices.

For example, in some configurations, the AC power frequency and the data carrier frequency differ by at least two orders of magnitude (100×) or, in other configurations, at least one order of magnitude (10×), thereby simplifying the design of filters 146 and 148. Using more complex modulation techniques such as quadrature modulation and at the price of increased circuit complexity, some configurations of the present invention transmit data using a carrier frequency the same as or very close to the power frequency.

Figure 7:
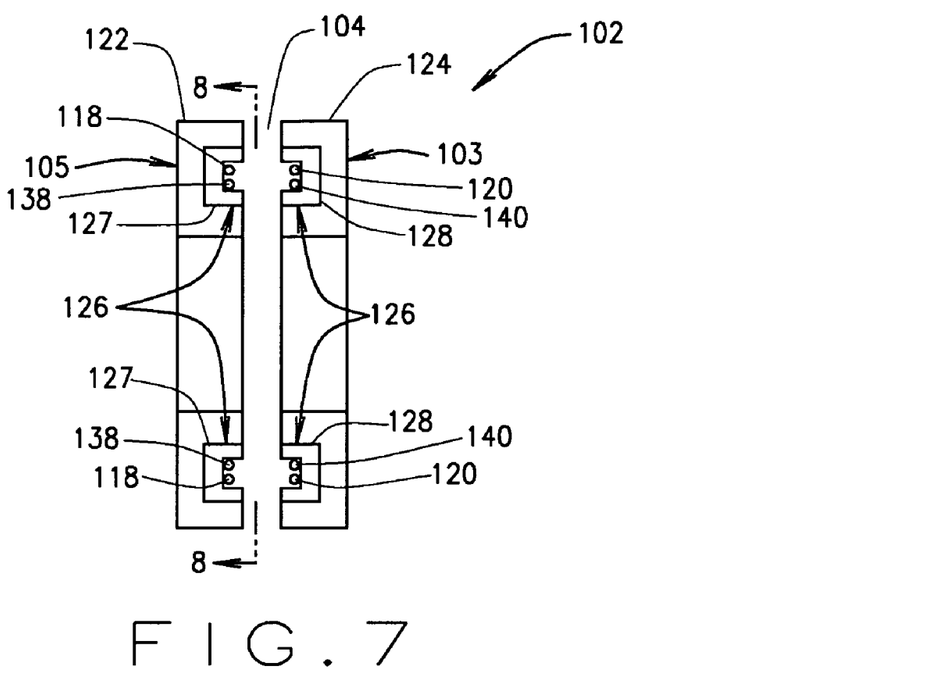
FIG. 7 is a sectional slice view of another configuration of rotary transformer.
Figure 8:
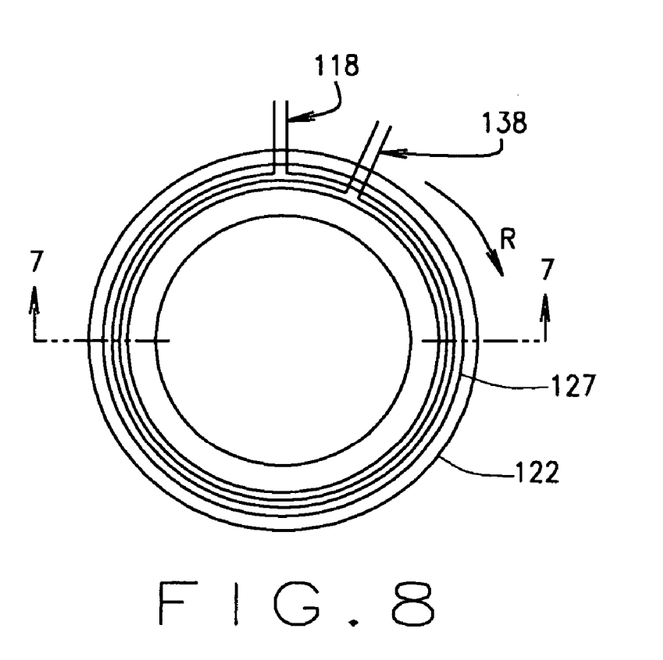
FIG. 8 is a view of one half of the rotary transformer of FIG. 7, taken along line 8-8 in FIG. 7. Line 7-7 is illustrative of a slice used to show the sectional slice view of FIG. 7.

In some configurations and referring to FIGS. 7 and 8, windings 118 and 138 are both wound within core portion 127, and windings 132 and 140 are wound within core portion 128. Because separate windings are used, core portions 127 and 128 in some configurations have E-shaped cross-sections with the power and the data windings separated in different grooves of the "E," although these configurations are not illustrated in FIGS. 7 and 8. In some configurations, holes and/or channels (not shown in FIG. 8) are provided in the magnetic core parts and/or the plastic rings to facilitate placement of the ends of the windings.

Figure 9:
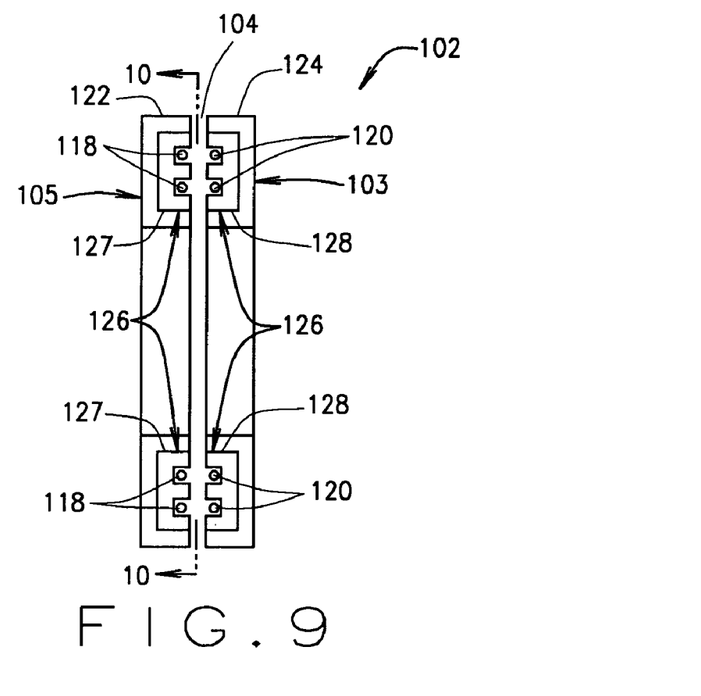
FIG. 9 is a sectional slice view of yet another configuration of rotary transformer.
Figure 10:
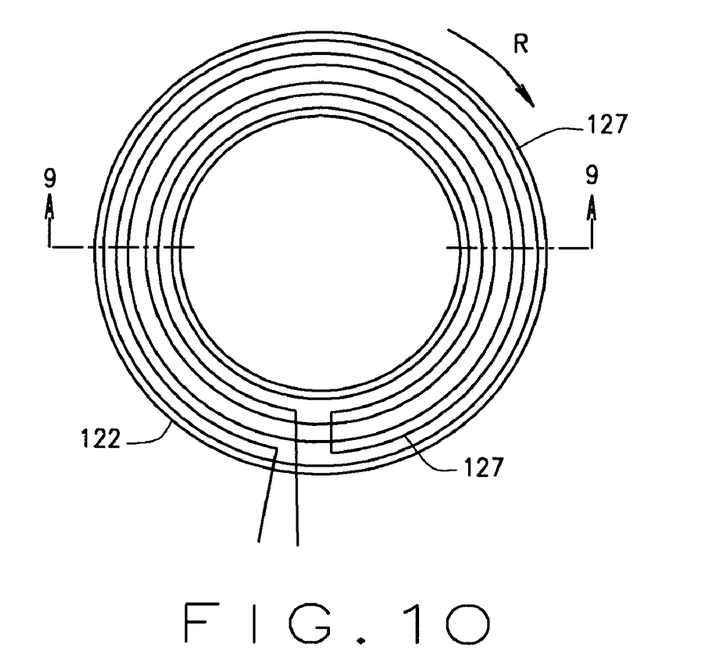
FIG. 10 is a view of one half of the rotary transformer of FIG. 9 in a slice similar to that taken for the transformer of FIG. 8.

In some configurations and referring to FIGS. 9 and 10, core portions 127 and 128 are provided with E-shaped cross sections. Core portions 127 and 128 comprise, for example, highly magnetically permeable material, such as ferrite. Winding 118 (and similarly, winding 120) enters a groove in E-shaped core portion 127 (and similarly, winding 120 enters a groove in E-shaped core portion 128), traverses the circumference of core portion 127, crosses over to the other groove, and traverses the circumference back to the input. By using E-shaped core portions and windings as shown, stray magnetic and electric fields are reduced, thereby reducing radiated emissions and coupling to other channels in a multiple channel system (not shown). Although only one turn is shown, multiple turns of wire on an E-shaped core portion may be used. In some configurations, a plurality of windings are placed in an E-shaped core to transfer power at a lower frequency.

Figure 11:
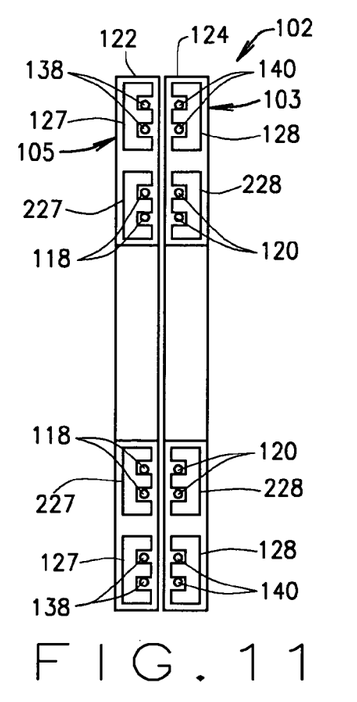
FIG. 11 is a sectional slice view of still another configuration of rotary transformer.
Figure 12:
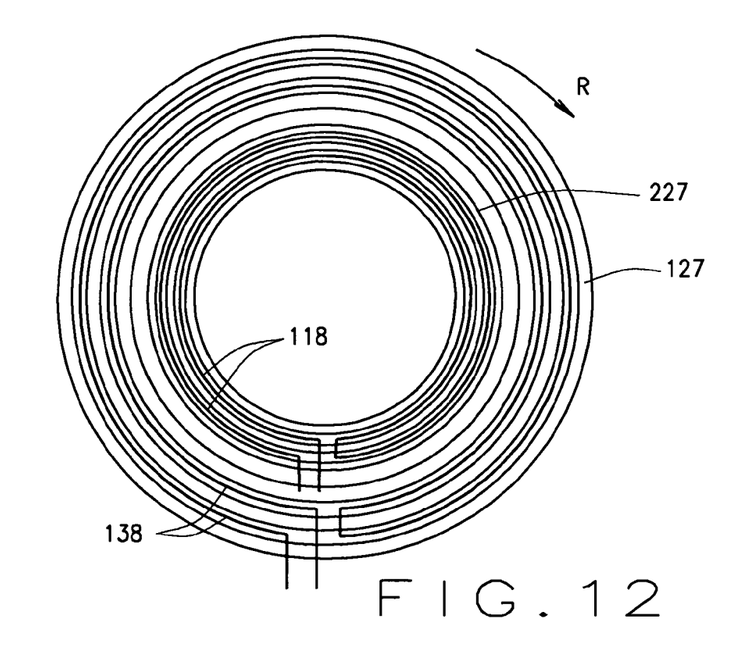
FIG. 12 is a view of one half of the rotary transformer of FIG. 11 in a slice similar to that taken for the transformer of FIG. 8.

In some configurations and referring to FIGS. 11 and 12, a plurality of core portions 127, 227 are used in ring 122 and a plurality of rings 128, 228 are used in ring 124. Core portion 127 includes a winding 138 that transfers power to a corresponding winding 140 in core portion 128 for applying power to components on the rotating side of transformer 102. Core portion 227 includes a winding 118 that transfers power to a winding 120 in core portion 228. The power applied to winding 118 is switched on and off and applied to X-ray source 14, which turns on and off accordingly.

Thus, and referring to FIGS. 1 through 12, some configurations of the present invention provide an imaging system 10, configured to acquire an image of an object 22 utilizing a rotating gantry 12. Imaging system 10 is, for example, a computed tomographic (CT) imaging system 10, but in other configurations is another type of imaging system, such as a magnetic resonance (MR) imaging system or ultrasonic imaging system. Imaging system 10 has a stationary electric system 110 (comprising, for example, DAS 32) and a rotating electronic system 112 (comprising, for example, detector array 18). Rotating electronic system 112 rotates with gantry 12. Imaging system 10 further includes a magnetically coupled rotary transformer 102, comprising rings 122 and 124. In some configurations, rings 122 and 124 have internal diameters larger than gantry opening 48 and are concentric with gantry 12, so that ring 122 rotates with gantry 12 and ring 124 is stationary from the frame of reference of FIG. 1. A gap 104 (which may be an air gap or a gap containing a nonmagnetic material) separates rings 122 and 124. Detector array 18, and hence, rotating electronic system 112, is (directly or indirectly) mechanically and electrically coupled to a rotating portion 105 of transformer 102. Stationary electronic system is (directly or indirectly) mechanically and electrically coupled to a stationary portion 103 of transformer 102. Data transmitted wirelessly between electronic systems 110 and 112 across rotary transformer 102 comprises image data from detector array 18.

In some configurations, at least one radio frequency modulator 114 is provided. Radio frequency modulator 114 is electrically and mechanically coupled to rotating portion 105 of transformer 102. At least one radio frequency demodulator 118 is provided that is electrically and mechanically coupled to the stationary portion 103 of transformer 102. Radio frequency modulator 114 is configured to modulate data from rotating electronic system 112 onto a carrier frequency, and radio frequency demodulator 118 is configured to demodulate the carrier frequency to recover the data for stationary electronic system 110, for example, to reconstruct an image of an object 22, as in FIG. 3. Amongst these configurations are configurations that also provide an additional modulator and demodulator, not shown in the Figures, to transmit data in the opposite direction, as well. In some configurations, power is also transmitted across gap 104, and in some of these configurations, separate power and data windings are provided in both the stationary 103 and rotating 105 portions of rotary transformer 102. For example, and referring to FIG. 6, stationary portion 103 of transformer 102 includes separate power winding 138 and data winding 118, and rotating portion 105 of transformer 102 includes separate power winding 140 and data winding 120. Some configurations also provide at least one filter (e.g., filter 148) configured to remove or reduce a power component on data windings 118, 120. The power component is provided, for example, by a power inverter 142 and recovered using power rectifier 144.

In some configurations, power is also coupled from a power supply in the stationary portion of imaging system 10 across rotary transformer 102 between electronic systems 110 and 112. For example, power can be provided to radiation source 14 in this manner. Data can also be coupled from the stationary portion of imaging system 10 to instruments on gantry 12. For example, commands to operate pre-patient collimators (not shown in the figures) or to configure detector array 18 can be transmitted across rotary transformer 102.

In some configurations, a data transmission system (not necessarily an imaging system) is provided that includes a transmitter 106, a receiver 108, and a magnetically coupled rotary transformer 102. Rotary transformer 102 comprises a first portion 105 and a second portion 103. First portion 105 of rotary transformer 102 includes a first portion 127 of a magnetic core 126. Second portion 103 of transformer 102 includes a second portion 128 of magnetic core 126. First and second portions 105 and 103 of transformer 102 are in moveable relationship with one another, hence, first and second portions 127 and 128 of magnetic core 126 are in moveable relationship with one another as well. Transmitter 106 is electrically and mechanically coupled to first portion 105 of transformer 102, and receiver 108 is electrically and mechanically coupled to second portion 103 of transformer 102. The data transmission system (106, 102, 108) is configured to wirelessly communicate data across rotary transformer 102 while the first and second portions 105 and 103 of transformer 102 are in relative motion. Amongst these configurations are configurations that also provide an additional transmitter and receiver, not shown in the Figures, to transmit data in the opposite direction, as well.

In some configurations, transmitter 106 further comprises a radio frequency modulator 114. Receiver 108 comprises a radio frequency demodulator 118. Radio frequency modulator 114 is configured to modulate data onto a carrier frequency and radio frequency demodulator 118 is configured to recover the data. The data transmission system further includes a power supply 142 and rotary transformer 102 is further configured to couple power from power supply 142 across the rotary transformer. In some configurations, a filter (e.g, filter 148) is provided to filter a power component from the carrier frequency coupled across rotary transformer 102. Some configurations further phase the carrier frequency with the data to reduce waveform jitter, and some configurations provide separate data and power windings (118 and 138, 120 and 140) in the first and second portions 105 and 103 of transformer 102.

Also, some configurations of the present invention provide a method for transferring data. The method includes electrically and mechanically coupling a first electronic system 112 to a first portion 105 of a magnetically coupled rotary transformer 102 and electrically and mechanically coupling a second electronic system 110 to a second portion 103 of rotary transformer 102. The method further includes wirelessly communicating data between first and the second electronic systems (112 and 110) across rotary transformer 102 while the first and second portions (105 and 103) of rotary transformer 102 are in relative motion.

In some configurations, wirelessly communicating data between first and the second electronic systems (112 and 110) further comprises modulating a carrier frequency with data, wirelessly transmitting the modulated carrier frequency across rotary transformer 102 while the first and second portions (105 and 103) of transformer 102 are in relative motion, and demodulating the modulated carrier frequency received across the rotary transformer. The method further includes magnetically coupling power from a power supply 142 across the rotary transformer simultaneously with the transmission of data, and filtering the modulated carrier frequency to reduce interference between the power and the data.

In some configurations, the carrier frequency is phased with the data to reduce waveform jitter.

Also, in some configurations, one of the electronic systems (e.g., 112) is mechanically coupled to a rotating gantry of an imaging apparatus 10 and the other electronic system (e.g., 110) is mechanically coupled to a stationary portion of imaging apparatus 10. Wirelessly transmitting data between electronic systems 112 and 110 in some of these configurations comprises transmitting image data, and the coupling of power from a power supply 142 across rotary transformer 102 further comprises coupling power from a stationary portion of imaging apparatus 10 to a rotating portion of imaging apparatus 10, e.g., radiation source 14.

In some configurations providing transmission of data in both directions, a transmitter and receiver on the same side of transformer 102 is configured as a transceiver.

It can thus be appreciated that service and repair costs of sliprings in imaging systems such as CT imaging systems 10 can be mitigated using various configurations of the present invention. Moreover, configurations of the present invention can also be used in other types of imaging systems, such as nuclear magnetic resonance (NMR) imaging systems and ultrasonic imaging systems, as well as many other types of electronic equipment (not necessarily imaging systems) in which data or data and power must be transmitted across a rotational interface.

While the invention has been described in terms of various specific embodiments, those skilled in the art will recognize that the invention can be practiced with modification within the spirit and scope of the claims.

What is claimed is:

1. An imaging system for acquiring an image of an object, the imaging system comprising:
   a rotating gantry;
   a stationary electronic system and a rotating electronic system that rotates with the rotating gantry;
   a magnetically coupled rotary transformer with a magnetic core having both a stationary portion and a rotating portion, the magnetic core including a data winding carried in a first groove and a power winding carried in the first groove;
   wherein the rotating electronic system is electrically and mechanically coupled to the rotating portion of the rotary transformer, and the stationary electronic system is electrically and mechanically coupled to the stationary portion of the rotary transformer, and wherein the rotating electronic system and stationary electronic system are configured to wirelessly communicate data modulated on a carrier frequency at a frequency different than that of electrical power transmitted across the rotary transformer.

2. A system in accordance with claim 1 further comprising a radio frequency modulator electrically and mechanically coupled to the rotating portion of the rotary transformer and a radio frequency demodulator electrically and mechanically coupled to the stationary portion of the rotary transformer, wherein the radio frequency modulator is configured to modulate data from the rotating electronic system onto a carrier frequency and the radio frequency demodulator is configured to demodulate carrier frequency to recover the data for the stationary electronic system.

3. A system in accordance with claim 2 having a separate data winding and a separate power winding in both the stationary portion and the rotating portion of the rotary transformer.

4. A system in accordance with claim 3 configured to transmit power between the power windings at a low frequency and to transmit data at a high carrier frequency.

5. A system in accordance with claim 4 wherein the frequency for transmitting power between the power windings is 200 kHz or less, and the frequency for transmitting data is 1 MHz or more.

6. A system in accordance with claim 4 further comprising at least one filter configured to remove or reduce a power component on the data windings.

7. A system in accordance with claim 1 further comprising a power supply, and further configured to couple power across the rotary transformer.

8. A system in accordance with claim 1 configured to wirelessly communicate the data across an air gap in the rotary transformer.

9. A system in accordance with claim 1 configured to phase a carrier with the data to reduce waveform jitter.

10. A system in accordance with claim 1 wherein the imaging system is a computed tomographic imaging system.

11. A data transmission system comprising:
    a transmitter;
    a receiver; and
    a magnetically coupled rotary transformer having a first portion and a second portion in moveable relationship with one another, the first portion including a first magnetic core, the first magnetic core including a data winding carried in a first groove and a power winding carried in the first groove, the second portion including a second magnetic core, the second magnetic core including a data winding carried in a second groove and a power winding carried in the second groove;
    wherein the transmitter is electrically and mechanically coupled to the first portion of the rotary transformer, and the receiver is electrically and mechanically coupled to the second portion of the rotary transformer, and wherein the transmitter and the receiver are configured to wirelessly communicate data modulated on a carrier frequency at a frequency different than that of electrical power transmitted across the rotary transformer while the first and the second portions of the rotary transformer are in relative rotary motion.

12. A system in accordance with claim 11 wherein the transmitter further comprises a radio frequency modulator and the receiver further comprises a radio frequency demodulator, and further wherein the radio frequency modulator is configured to modulate data onto a carrier frequency and the radio frequency demodulator is configured to demodulate the modulated carrier frequency to recover the data, and the data transmission system further comprises a power supply, and the rotary transformer is further configured to couple power from the power supply across the rotary transformer.

13. A system in accordance with claim 12 further comprising a filter configured to filter a power component from the carrier frequency coupled across the rotary transformer.

14. A system in accordance with claim 12 further configured to phase the carrier frequency with the data to thereby reduce waveform jitter.

15. A system in accordance with claim 12 having a separate data winding and a separate power winding in each of the first and second portions of the rotary transformer.

16. A method for transferring data comprising:
electrically and mechanically coupling a first electronic system to a first portion of a magnetically coupled rotary transformer, the first portion including a first magnetic core, the first magnetic core including a data winding carried in a first groove and a power winding carried in the first groove;
electrically and mechanically coupling a second electronic system to a second portion of the rotary transformer, the second portion including a second magnetic core, the second magnetic core including a data winding carried in a second groove and a power winding carried in the second groove; and
wirelessly communicating data modulated on a carrier frequency at a frequency different than that of electrical power transmitted between the first and the second electronic systems across the rotary transformer while the first and the second portions of the rotary transformer are in relative motion.

17. A method in accordance with claim 16 wherein said wirelessly communicating data between the first and second electronic systems further comprises modulating a carrier frequency with data, wirelessly transmitting the modulated carrier frequency across the rotary transformer while the first and the second portions of the rotary transformer are in relative motion, and demodulating the modulated carrier frequency received across the rotary transformer, and said method further comprises magnetically coupling power from a power supply across the rotary transformer simultaneously with said wireless communication of data, and filtering the modulated carrier frequency to reduce interference between the power and the data.

18. A method in accordance with claim 17 further configured to phase the carrier frequency with the data to thereby reduce waveform jitter.

19. A method in accordance with claim 18 wherein one of the electronic systems is mechanically coupled to a rotating gantry of an imaging apparatus and the other of the electronic systems is mechanically coupled to a stationary portion of the imaging apparatus, and wherein said wirelessly communicating data between the first and the second electronic systems further comprises transmitting image data, and said coupling power from a power supply across the rotary transformer further comprises coupling power from a stationary portion of the imaging apparatus to a rotating portion of the imaging apparatus.

20. A method in accordance with claim 16 wherein at least one of the electronic systems is mechanically coupled to a rotating gantry of an imaging apparatus, and wherein said wirelessly communicating data between the first and the second electronic systems further comprises transmitting image data between the first and the second electronic systems.

* * * * *